United States Patent [19]

Dixon

[11] Patent Number: 4,722,728
[45] Date of Patent: Feb. 2, 1988

[54] NEEDLELESS HYPODERMIC INJECTOR

[75] Inventor: Alan J. Dixon, Charlottetown, Canada

[73] Assignee: Patents Unlimited, Ltd., Hamilton, Bermuda

[21] Appl. No.: 6,157

[22] Filed: Jan. 23, 1987

[51] Int. Cl.[4] ............................................. A61M 5/30
[52] U.S. Cl. ..................................................... 604/68
[58] Field of Search ............................. 604/68, 70, 71

[56] References Cited

U.S. PATENT DOCUMENTS

| | | | |
|---|---|---|---|
| 2,398,544 | 4/1946 | Lockhart | 604/68 |
| 2,704,543 | 3/1955 | Scherer | 604/68 |
| 2,754,818 | 7/1956 | Scherer | 604/68 |
| 2,762,370 | 9/1956 | Venditty | 604/68 |
| 2,816,543 | 12/1957 | Venditty et al. | 604/68 |
| 2,816,544 | 12/1957 | Scherer et al. | 604/68 |
| 4,623,332 | 11/1986 | Lindmayer et al. | 604/68 |

FOREIGN PATENT DOCUMENTS 772968 4/1957 United Kingdom .
1333215 10/1973 United Kingdom .

Primary Examiner—John D. Yasko
Attorney, Agent, or Firm—Wegner & Bretschneider

[57] ABSTRACT

A needleless hypodermic injector has a first substantially cylindrical section and a second substantially cylindrical section movably mounted in a first end of the first section. The first section comprises a hollow cylinder defining a chamber for a substance to be administered, the chamber having therein an externally communicating orifice at a second end of the first section and a piston slidably mounted in the hollow cylinder. The second section comprises spring means in the form of a coil spring and a plurality of disc springs arranged in an axial row for driving the piston in the first section from a retracted position in which the hollow cylinder contains the substance to be administered to an extended position in which the substance is substantially completely discharged through the orifice from the chamber. A bushing is slidably mounted between the piston and the spring means and is capable of engaging the piston as it travels from the retracted position to the extended position. Latch means are also provided for locking the bushing and thereby the compressed spring means in the retracted position. With the above arrangement, when the latch means is released from the bushing, the compressed spring means rapidly impacts the bushing against the piston to provide a first, high skin piercing pressure to the substance to be discharged through the orifice and thereafter moves the piston to the extended position at a second, lower discharge pressure. The coil spring remains under substantial compression at the extended position and sufficient disc springs are present to absorb recall energy caused by the piston bushing suddenly reaching the extended position.

11 Claims, 6 Drawing Figures

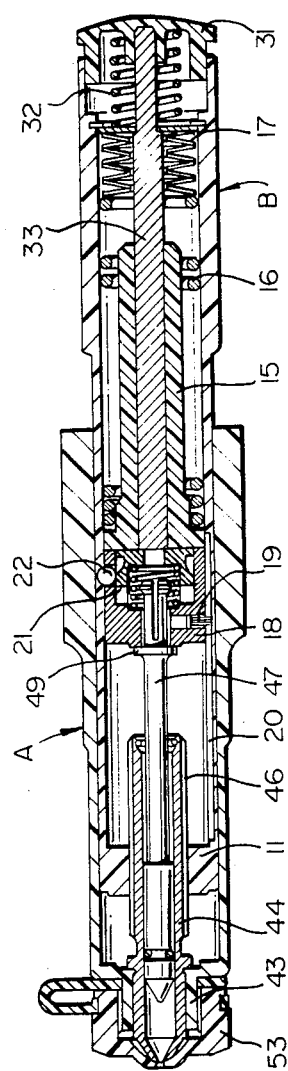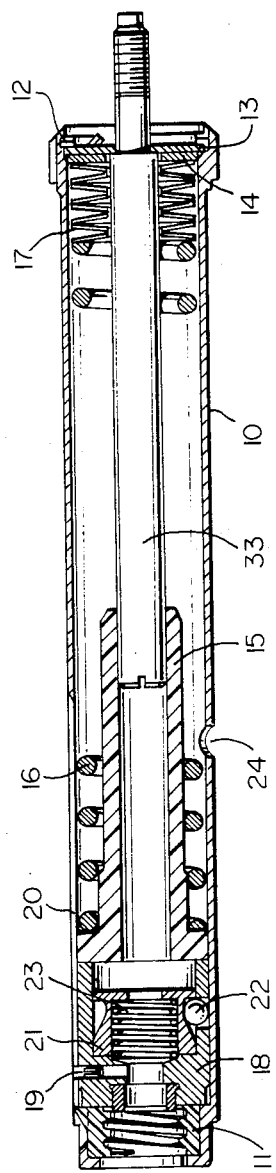
FIG.1
FIG.2

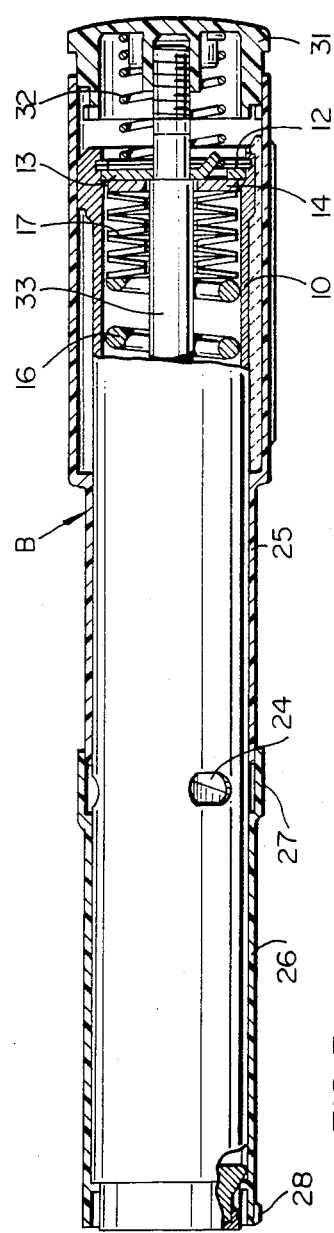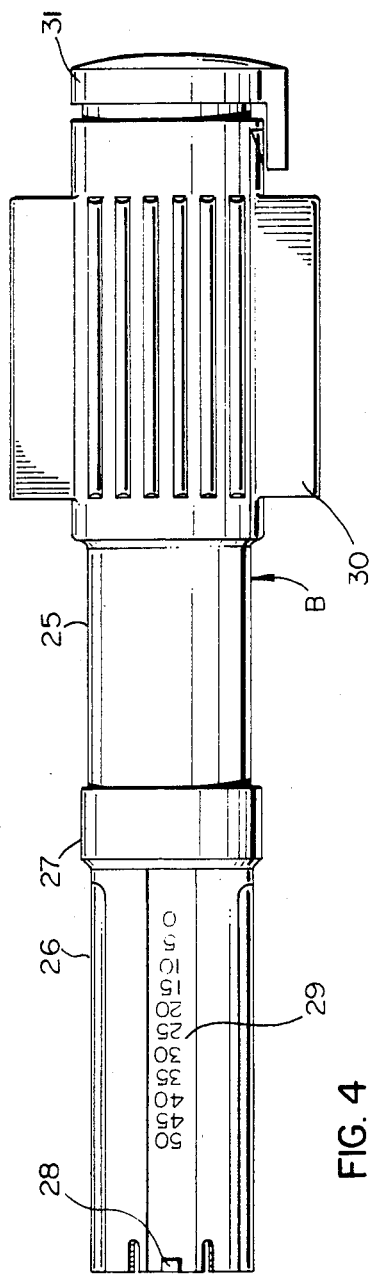

NEEDLELESS HYPODERMIC INJECTOR

BACKGROUND OF THE INVENTION

This invention relates to a needleless hypodermic injector, and more particularly a spring-powered needleless injector.

There is a widespread interest in the use of needleless injectors for the injection of medicines into the body of both humans and animals. A needleless jet injector makes a substantially smaller hole than does a needle, and consequently needleless injection is less painful than injection with a needle. Moreover, for people requiring frequent injections, e.g., diabetics, needleless injection has the important advantage of causing less damage to the skin and tissue. This is very significant, since the areas on the body which can be used for injection are limited.

The typical needleless hypodermic injector is adapted to discharge a liquid medicine from an orificed cylinder in the form of a minute stream or jet at two different pressure stages sequentially. The initial high pressure discharge causes the jet stream to distend the skin and force the liquid to a predetermined depth beneath the surface, depending upon the magnitude of the pressure. After the minute opening in the epidermis has been produced, the pressure of the stream is immediately reduced to a lower second stage for completing transfer of the remaining liquid from the cylinder.

Such devices have been known for more than forty years and, for instance, a typical two-stage hypodermic jet injector is described in U.S. Pat. No. 2,398,544. Many other patents have also issued over the years describing various forms of needleless injectors. Few of the devices disclosed by these patents are available in the marketplace. Many of the patented devices lack simplicity and are too expensive to produce or use.

While the concept of the needleless injector is quite simple, there have been many problems in its practical usage. Thus, the injector must be compact and light and very simple to use while, at the same time, being capable of generating very high pressures. For instance, the initial high pressure discharge is usually at a pressure of in excess of 700 kg/cm$^2$ and the lower second stage is typically at a pressure in the order of 200 kg/cm$^2$. If any substantial volume of medicine is to be discharged by such device, it becomes evident that a very high spring pressure will be necessary. It is also important that a substantial pressure be maintained throughout the entire injection.

An important advance in needleless jet injectors is described in Lindmayer, et al, U.S. Pat. No. 4,623,332 issued Nov. 18, 1986. This is a very compact needleless jet injector in which the spring drive comprises a series of axially aligned disc springs adapted to move an injector piston such that the discharge pressure remains substantially constant or increasing throughout the injection following the initial high pressure skin piercing stage. While that device worked quite well, it also had certain difficulties. For instance, a large number of disc springs were necessary, making the injector somewhat heavy and there were also difficulties in obtaining uniformity of compression load in the disc springs.

It is, therefore, the object of the present invention to find a modified form of spring action which will overcome the difficulties of the disc springs described in U.S. Pat. No. 4,623,332.

SUMMARY OF THE INVENTION

This invention is an improvement to the injector of U.S. Pat. No. 4,623,332. In trying to overcome the above problems associated with the use of disc springs as the power source, a strong coil spring was tried in place of the disc springs. It was found that the pressures necessary for a satisfactory two-stage jet injection could be achieved with a simple coil spring mounted to have a high axial force of up to about 45 kg, preferably at least 41 kg, when compressed and a residual axial force of at least about 18 kg when extended. However, because of its very compact design, the entire injector had a weight of less than about 200 grams and it was found that when the injection was completed, there was a bounce or recoil in the injector which was not acceptable. In searching for a solution to the bounce or recoil problem, it was surprisingly discovered that the bounce or recoil could be totally eliminated if a recoil or shock absorber were mounted at one end of the coil spring.

Thus, the present invention in its broadest aspect relates to a needleless hypodermic injector having a first substantially cylindrical section and a second substantially cylindrical section movably mounted in a first end of the first section. The first section comprises a hollow cylinder defining a chamber for a substance to be administered, the chamber having therein an externally communicating orifice at a second end of the first section and a piston slidably mounted in the hollow cylinder. The second section comprises spring means in the form of a coil spring with a shock absorber at one end thereof for driving the piston in the first section from a retracted position in which the hollow cylinder contains the substance to be administered to an extended position in which the substance is substantially completely discharged through the orifice from the chamber. A bushing is slidably mounted between the piston and the spring means and is capable of engaging the piston as it travels from the retracted position to the extended position. Latch means are also provided for locking the bushing and thereby the compressed spring means in the retracted position.

With the above arrangement, when the latch means is released from the bushing, the compressed spring means rapidly impacts the bushing against the piston to provide a first, high skin piercing pressure to the substance to be discharged through the orifice and thereafter moves the piston to the extended position at a second, lower discharge pressure. The coil spring remains under substantial compression at the extended position and the shock absorber is able to absorb recoil energy caused by the piston and bushing suddenly reaching the extended position.

The shock absorber must be capable of totally absorbing the bounce or recoil energy resulting from the coil spring being very suddenly stopped at the end of the injection while still being under substantial residual compression, i.e. at least 18 kg. A polyurethane rubber pad or a specially designed coil spring or a series of disc springs may be used for this purpose. The disc springs have been found to work very well.

The injection orifice has a diameter of less than about 0.3 mm, preferably about 0.1–0.2 mm in order to inject a jet with minimum discomfort. Also for minimum bruising of the skin and minimum discomfort during the injection, the spring means should generate an axial force when compressed of about 41–45 kg and a residual axial force of at least about 18 kg when extended. With such axial force and orifice size, it will be evident that the substance being injected travels through the orifice under great pressure and at great speed. Typically, a 0.5 cc injection is totally injected through the orifice within a time of less than 250 milliseconds, and when using a 0.2 mm orifice the injection time may be as little as 100 milliseconds. In order to have a very uniform jet of liquid under the above conditions, it has been found to be particularly advantageous to form the orifice in a synthetic gem material, such as a synthetic ruby or sapphire.

BRIEF DESCRIPTION OF THE DRAWINGS

The invention will now be described in greater detail with reference to the accompanying drawings, which illustrate preferred embodiments and wherein:

FIG. 1 is a longitudinal, sectional view of the injector in retracted position;

FIG. 2 is a longitudinal, sectional view of the injector power pack assembly;

FIG. 3 is a side elevation in partial section of the fully assembled power pack;

FIG. 4 is a top plan view of the power pack of FIG. 3;

Figure 5:
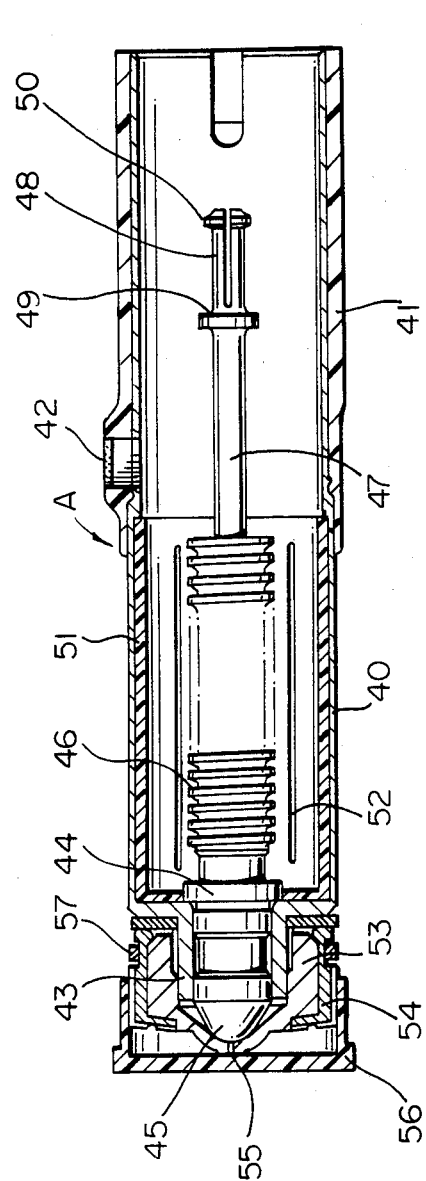
FIG. 5 is a longitudinal, sectional view of the injector portion.

As can be seen from the drawings, the injector of the invention includes a hollow cylindrical front section A and a hollow cylindrical rear section B. The front section is the injector portion and the rear section is the power pack assembly.

The rear section B is the principle novel feature of this invention and is preferably formed with an inner stainless steel sleeve 10 which retains the power mechanism. The lower end of sleeve 10 has an internally threaded collar 11 and the upper end of steel sleeve 10 is closed by means of a spring lock washer 13 held in place by retaining ring 12. Beneath spring lock washer 13 is a further washer 14.

Within steel sleeve 10 is a spring chamber which contains a coil spring 16 and a series of disc springs 17. The lower end of coil spring 16 is preferably held in position laterally by means of an annular spring guide 15.

Immediately below the spring guide 15 is located a slideable cup-shaped lock bushing 18 having a bottom wall with an axial opening therein. It also includes in the side wall thereof several holes each containing a hard ball 22 and a pin 19 extending into a groove 20 in sleeve 10 to permit sliding of the bushing within the sleeve without rotation.

Within the cup-shaped bushing 18 is a lock collar 21 with an inclined shoulder portion in the side wall thereof. This shoulder acts as a cam in relation to the balls 22 and the shoulder is biased against the balls 22 by means of coil spring 23. The tube wall 10 also includes holes 24 adapted for engaging with the balls 22. Extending through the top end of sleeve 10 and axially through the springs and axially through the spring guide is a release pin 33.

As will be seen from FIGS. 3 and 4, the steel sleeve of FIG. 2 is encased in a plastic sheath. This includes an upper sheath portion 25 and a lower sheath portion 26. These are joined by an axially offset collar 27 which provides an annular space adjacent the holes 24 in tube 10. The lower end of the plastic sheath 26 includes small projecting tabs 28 and it also includes a series of numerals 29. The upper plastic sheath 25 includes projecting wings 30 providing convenient means for gripping the actuator. The upper end of the device includes a release button 31 attached to the end of release pin 33 and being spring biased axially outwardly by means of coil spring 32.

Figure 6:
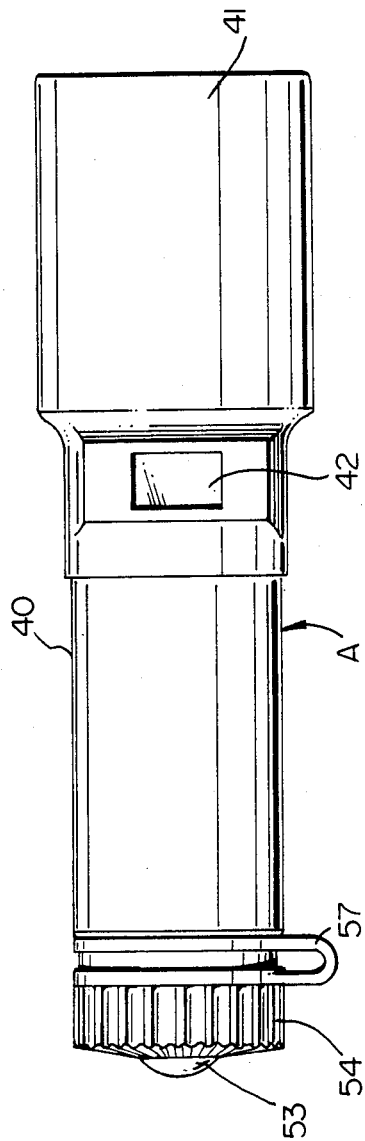
FIG. 6 is a top plan view of the injector portion of FIG. 5.

As can be seen from FIGS. 5 and 6, the injector portion A also includes a stainless steel sleeve portion 40 having an externally threaded axial neck 43 at the lower end and having an open top end. A cylinder assembly 44 for the medicine to be discharged is mounted within the neck 43 and the cylinder has a rounded end tip 45 with an axial orifice therein. The cylinder assembly 44 includes an external thread 46 and mounted within the cylinder is a piston 47. This piston has an impact collar 49 formed in an upper portion thereof and its outer end is bifurcated by means of a longitudinal slot. Finally, the outer tip includes an enlarged portion 50. Mounted within steel sleeve 40 is an inner plastic sleeve 51 with grooves 52 therein. The outer face of steel sleeve 40 includes a plastic cover 41 with gripping wings and a lens 42 for viewing the numerals 29.

The bottom end of the injector portion includes a nozzle cap 53 with an orifice 55 and surrounded by a plastic collar 54. The orifice 55 is preferably formed within a synthetic gem which is pressed into an axial opening in the nozzle cap, with preferred diameters for the orifice being 0.15 mm or 0.2 mm. The nozzle cap is retained with the injector by means of retainer strap 57. Finally there is provided a protective cover 56 for the nozzle cap.

The separate nozzle cap 53 is an important feature of the device. The inner face of the cap is concave and this concave face smoothly mates with the convex end face of rounded end tip 45 of cylinder assembly 44. The axial orifice in end tip 45 is usually somewhat larger in diameter than orifice 55 in cap 53 and with the nozzle cap in place, the two orifices are axially aligned with a tight seal being formed between the concave face and the convex face adjacent the orifices. When the nozzle cap 53 is removed for drawing medicine into the cylinder, the larger diameter of the orifice in the end tip 45 provides for easier loading and the nozzle cap has protected the end tip 45 from contamination.

The specific device shown has a body diameter of about 20 mm, excluding the gripping wings, a length of about 175 mm and a weight of about 170 grams.

Method of Use

When the cylindrical sections A and B are connected as shown in FIG. 1, the rear section B is screwed into the front section A until the piston 47 is at the lower end of the cylinder 44. The end of the piston 47 then snaps through the hole in the bottom wall of lock bushing 18 in the manner shown in FIG. 1. Continued twisting action of the upper section B with respect to the lower section A compresses the springs until the balls 22 come into alignment with the wall recesses 24. At this point, the cam shoulder of the lock collar 21 forces the balls outwardly into the recesses 24. This serves to lock the mechanism in the loaded position.

Next, the nozzle cap is removed and a medicine vial and adaptor are connected to the threading 43. With the medicine vial in place, the rear section B is twisted in the reverse direction so that the piston 47 is pulled rearwardly, drawing medicine from the vial into the cylinder 44. When the appropriate dosage has been loaded as indicated in the lens 42, the twisting in the loading direction is stopped. Then the rear section B is given several turns in the reverse direction to provide a desired initial impact gap. This is a gap between the bottom of bushing 18 and the impact shoulder 49, which creates the high initial skin piercing pressure when the injector is fired. To aid in easily determining the amount of turning necessary to obtain the desired dosage and/or impact gap, the projecting tabs 28 on rear section B and the internal grooves 52 in front section A may be used. When the rear section is twisted with respect to the front section, the tabs 28 engage the grooves 52, causing a clicking. Thus, the dosage and/or impact gap may be set by rotating a predetermined number of "clicks".

The medicine vial and adaptor are then removed from neck 43 and the nozzle cap 53 is installed. To perform an injection, the nozzle cap is held in a perpendicular position to the skin. Then the release button 31 is pushed downwardly, thereby pushing the release rod against lock collar 21 pushing it downwardly and thereby releasing the balls 22 from the locking recesses 24 and firing the mechanism.

I claim:

1. A needleless hypodermic injector, comprising:
   a first substantially cylindrical section and a second substantially cylindrical section movably mounted in a first end of the first section;
   said first section comprising a hollow cylinder defining a chamber for a substance to be administered, the chamber having therein an externally communicating orifice at a second end of the first section, and a piston slidably mounted in the hollow cylinder;
   and the second section comprising spring means in the form of a coil spring with a shock absorber at one end thereof for driving the piston in the first section from a retracted position in which the hollow cylinder contains the substance to be administered to an extended position in which the substance is substantially completely discharged through the orifice from the chamber; a bushing slidably mounted between the piston and the spring means, and capable of engaging the piston as it travels from the retracted position to the extended position; and latch means for locking the bushing and thereby the compressed spring means in the retracted position;
   whereby, when the latch means is released from the bushing, the compressed spring means rapidly impacts the bushing against the piston to provide a first, high skin piercing pressure to the substance to be discharged through the orifice and thereafter moves the piston to the extended position at a second, lower discharge pressure, with the coil spring remaining under substantial compression at the extended position and the shock absorber absorbing the recoil energy caused by the piston and bushing suddenly reaching the extended position.

2. The injector of claim 1, wherein the shock absorber is mounted within a chamber with the coil spring, with the shock absorber being located at the end of the coil spring remote from the piston-engaging bushing.

3. The injector of claim 2, wherein the shock absorber comprises a plurality of disc springs arranged in an axial row at an end of the coil spring.

4. The injector of claim 3, wherein the shock absorber comprises a pad of polyurethane rubber at an end of the coil spring.

5. The injector of claim 1, wherein the spring means provides an axial force of up to about 45 kg in the retracted position and at least about 18 kg in the extended position.

6. The injector of claim 5, wherein the spring means provides an axial force of about 41–45 kg in the retracted position.

7. The injector of claim 5, wherein the orifice has a diameter of less than 0.3 mm and the hollow cylinder holds no more than about 0.5 cc of substance to be administered.

8. The injector of claim 7, wherein the orifice has a diameter of about 0.15–0.2 mm, the hollow cylinder holds no more than about 0.5 cc of substance to be administered and the spring means generates discharge pressures sufficient to inject up to 0.5 cc of said substance within a time of less than 250 milliseconds.

9. The injector of claim 2, wherein the entire injector weighs less than about 200 grams.

10. The injector of claim 2 wherein the injection orifice is in a synthetic gem, the orifice having a diameter of about 0.15–0.2 mm.

11. The injector of claim 9 having a cylindrical body diameter of less than 25 mm and an assembled length of less than 180 mm.

* * * * *